United States Patent [19]

Ueyama et al.

[11] Patent Number: 4,476,389
[45] Date of Patent: Oct. 9, 1984

[54] EMISSION TYPE COMPUTED TOMOGRAPHY APPARATUS

[75] Inventors: Akihide Ueyama; Nobuo Kumano, both of Tochigi; Hidetomo Takase, Yaita, all of Japan

[73] Assignee: Tokyo Shibaura Denki Kabushiki Kaisha, Kawasaki, Japan

[21] Appl. No.: 301,437

[22] Filed: Sep. 11, 1981

[30] Foreign Application Priority Data

Sep. 17, 1980 [JP] Japan .................... 55-129916

[51] Int. Cl.³ .............................. G01T 1/20
[52] U.S. Cl. ................................ 250/363 S
[58] Field of Search ............ 250/361 R, 363 R, 363 S; 378/11, 12, 13, 15, 17, 20

[56] References Cited

U.S. PATENT DOCUMENTS

| | | | |
|---|---|---|---|
| 3,432,660 | 3/1969 | Anger | 250/363 S |
| 3,970,853 | 7/1976 | Kuhl et al. | 250/363 S |
| 4,057,726 | 11/1977 | Jaszczak | 250/363 S |
| 4,181,939 | 1/1980 | Lyons . | |
| 4,216,381 | 8/1980 | Lange | 250/363 S |
| 4,220,861 | 9/1980 | Colombo et al. | 250/363 S |
| 4,368,389 | 1/1983 | Blum | 378/20 |

FOREIGN PATENT DOCUMENTS 014,339 1/1980 European Pat. Off.
1,565,183 4/1980 United Kingdom .

*Primary Examiner*—Janice A. Howell
*Attorney, Agent, or Firm*—Cushman, Darby & Cushman

[57] ABSTRACT

An emission type computed tomography apparatus comprises a mechanism for rotating a detector along a circle centered at a human body to whom radioisotope is previously given, and a circuit for reconstructing a tomogram in accordance with an output signal from said detector. The rotating mechanism further has a member for slanting the detector with respect to a tangential line of the circle, a member for slanting said detector with respect to the body axis, and a member for changing the radius of the rotating circle of the detector.

2 Claims, 5 Drawing Figures

EMISSION TYPE COMPUTED TOMOGRAPHY APPARATUS

BACKGROUND OF THE INVENTION

The present invention relates to an emission type computed tomography (CT) apparatus.

Recently, an emission type CT apparatus has been developed in which γ rays emitted from radioisotope given to an organism are detected and a tomogram is reconstructed on the basis of an RI distribution within the organism. From a safety viewpoint, the emission type CT is advantageous since no X rays are radiated into the organism, but has in a poor field ratio. The reason for the disadvantage is that a γ ray detector of the emission type CT can detect only the γ rays projected orthogonally to a detecting surface, that is to say, a field of the detector is confined within the same area as the detecting surface. When the detector rotates in a plane containing a cross section of the organism, the detecting surface is generally in parallel with an axis of the organism, including a tangential line of a locus circle of the rotation. A tomogram of a cross section of the organism obtained is always within a circle area with a diameter equal to the width of the cross sectional area of the detector. For this reason, in order to obtain tomogram of cross sectional areas of a head and an abdomen of a human body by the same detector, the width of the cross sectional area of the detector must be made large conforming to the size of the abdomen. This measure, however, is unadvisable because the detector with a large field is expensive and a drive mechanism for driving it is made large in size, then the CT apparatus is made large in size with poor handling of the apparatus.

Also for obtaining a longitudinal tomogram along a body axis of a human body, the following problem arises. For taking a longitudinal tomogram of the entire abdomen longer than a length of the longitudinal width of the detector, the human body or the detector must be moved along the body axis by several scannings. This is a time consuming work and needs an additional moving mechanism.

SUMMARY OF THE INVENTION

Accordingly, it is an object of the present invention to provide a small-sized emission type computed tomography apparatus which can substantially enlarge a field of a detector and obtain a tomogram of a wide area for a short time.

The above object is obtained by an emission type computed tomography apparatus which comprises a detector for producing a signal representing radiation projected into a detecting surface, a holding member for holding a detector of which the detecting surface can be inclined at a given angle to a tangential line of a circle of the center of a body axis ranging from a head to foot of an organism, a rotating member for rotating circularly the detector about the body axis by means of the holding member, and a processing circuit for obtaining the tomography information of the entire organism by processing an output signal produced from the detector when the detector circularly rotates by means of the rotating member.

DETAILED DESCRIPTION OF THE PREFERRED EMBODIMENT

Figure 1:
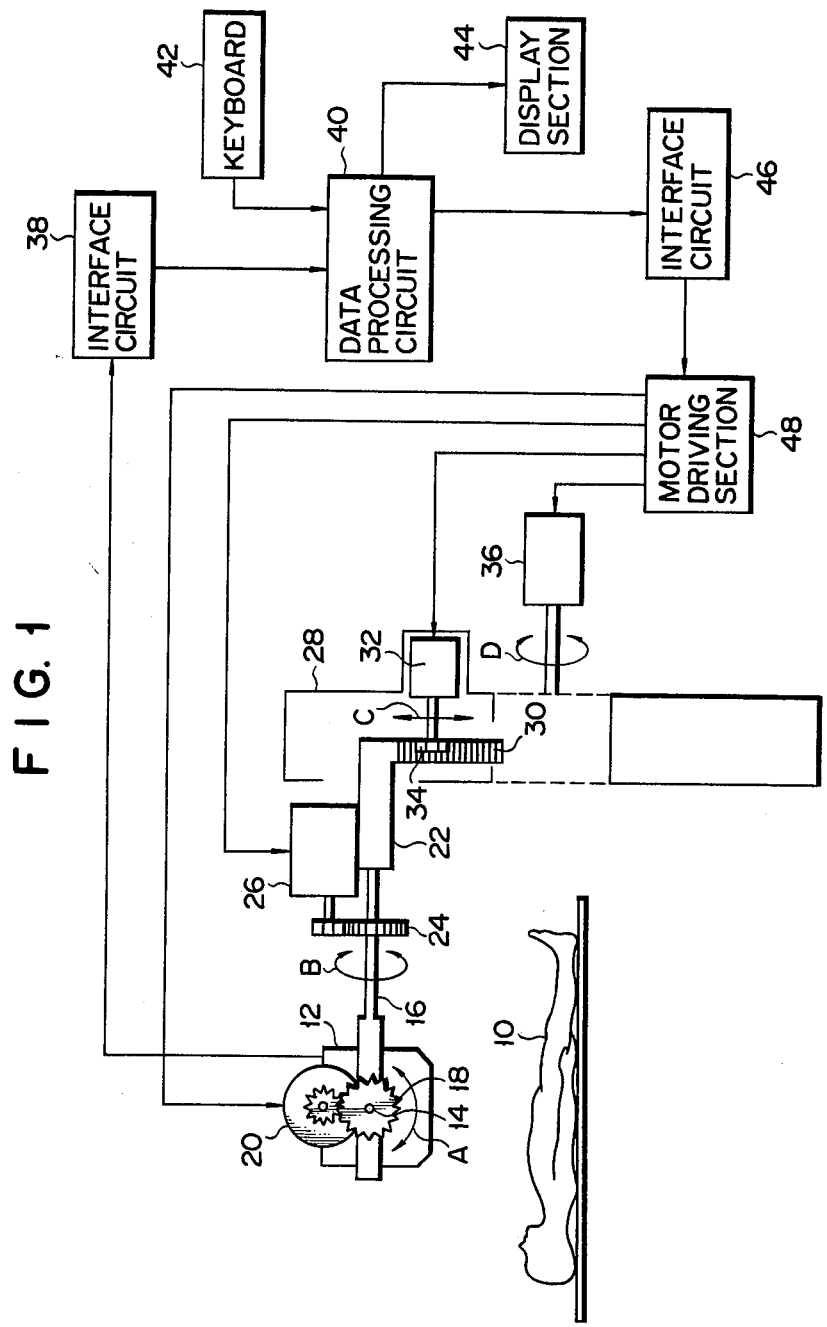
FIG. 1 shows, by way of block and schematic diagram, an emission type computed tomography apparatus of an embodiment according to the present invention.

An embodiment of an emission type CT apparatus according to the present invention will be described referring to the accompanying drawings. In FIG. 1 as a block diagram of the CT, a detector 12 is disposed above a human body 10 as an object to be tomographed. Before diagnosis, radioisotope is given to the human body 10. Although not shown, a collimator is mounted on a detecting surface of the detector 12 as an anger type gamma camera.

The detector 12 is rotatably mounted to a Y-shaped arm 16 by means of a pin 14 and is rotatable in the direction of an arrow A. A gear 18 is attached to the pin 14. A rotation of a motor 20 mounted to a part of the Y-shaped arm 16 is transferred through the gear 18 to the pin 14 and the rotation about the pin 14 of the detector 12 is controlled by the motor 20. An end of the Y-shaped arm 16 is mounted to a holding arm 22 and is rotatable in the direction of an arrow B. A rotation of the motor 26 mounted to the part of the holding arm 22 is transferred to the Y-shaped arm 16 of which the rotation is controlled by the motor 26. The holding arm 22 is mounted to a ring-shaped rotating rack 28 in a manner that it is movable in the radial direction of the rack, i.e. in the direction of an arrow C. The holding arm 22 is provided with a pinion section 30. A rotation of a motor 32 provided at the part of the rotating rack 28 is transferred through a rack gear 34 to the pinion section 30 and the movement of the holding arm 22 is under control of the motor 32. The rotating rack 28 is mounted at the center to the axis of a motor 36 and is rotatable about the body axis from the head to the foot of the human body 10 in the direction of an arrow D.

An output signal from the detector 12 which represents a dosage of γ rays emitted from the human body 10 is supplied to a data processing circuit 40 by way of an interface circuit 38. A signal from a keyboard 42 is also supplied to the data processing circuit 40. An output signal from the data processing circuit 40 is applied to a display section 44 and to a motor driving section 48 via an interface circuit 46. An output signal from the motor driving section 48 is supplied to the motors 20, 26, 32 and 36.

The operation of the embodiment as mentioned above will be described. A case where a tomogram of a cross section orthogonal to a body axis ranging from the head to foot of the human body 10 is obtained will first be described. The detecting surface of the detector 12 is circular and its diameter is wider than a lateral length of the average head, but is smaller than the half of a lateral length of the abdomen. For taking the tomogram of the head, the detector 12 is mounted to the Y-shaped arm 16 and the holding arm 22 in a manner that the detecting surface of the detector 12 is aligned in parallel with the body axis and includes a tangential line of the ring of the rotating rack 28, and then rotating rack 28 is rotated. In this way, a dosage of the γ radiation, in all the radial directions, of all the picture elements in the cross section of the head can be detected, thereby obtaining the tomogram of the head.

Figure 2:
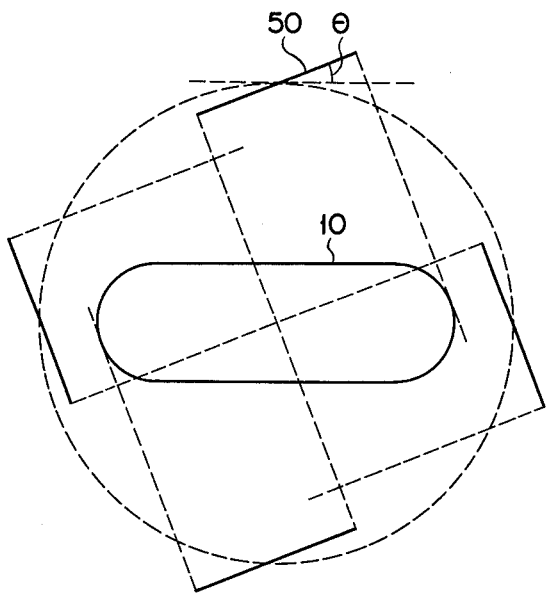
FIGS. 2 to 5 schematically illustrate positional relations of a human body to a detector, which is useful in explaining the operation of the embodiment as shown.

The cross sectional area of the abdomen, however, is larger a field of the detector 12, i.e. a circular area equal to the detector 12. Therefore, this method can obtain a tomogram of only a part of the abdomen. If the detector 12 is inclined at an angle $\theta$ with respect to the tangential line of the circular locus of the rotation of the detecting surface 50, as shown in FIG. 2, before the detector 12 is rotated about the human body 10 together with the rotating rack 28, the entire of the cross sectional area of the human body 10 falls within the field (indicated by a broken line) of the detector 12. Therefore, even with the detector having a narrow field, a tomogram with a large cross section can be obtained, with the result that the tomograms of the head and the abdomen can be obtained by using the same detector.

Figure 3:
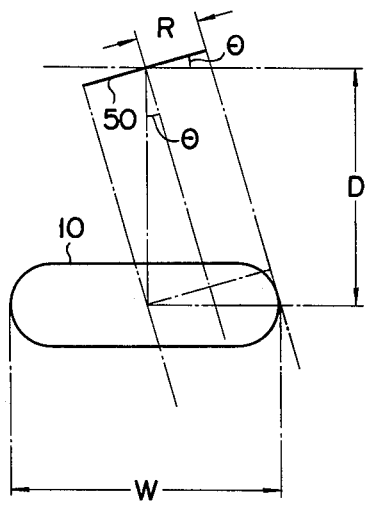

The inclination angle $\theta$ of the detector 12 can be determined directly with the eye by rotating the motor 26 through the operation on the keyboard 42 and rotating the Y-shaped arm 16 in the B direction shown in FIG. 1. This can of course be set to an optimum value in an automatical manner. The automatic method will be discussed referring to FIG. 3. A magnitude of the angle $\theta$ changes depending on a distance between the detector 12 and the human body 10, i.e. a radius D of the rotating circular of the detector 12. Therefore, the distance D must be set firstly. If the width of the human body 10 is assumed to be W, the distance D must be W/2 or more. Therefore, the distance D is selected such that a relation $2D = 1.1 W \ldots (1)$ holds sufficiently. The abdomen width of the human body 10 is keyed from the keyboard 42 into the data processing circuit 40. The data processing circuit obtains the data D by using the equation (1) and supplies the data D through the interface circuit 46 to the motor drive circuit 48 thereby to drive the motor 32. As a result, the holding arm 22 is moved in the direction of the arrow C shown in FIG. 1 to determine the distance D. When the half of the width of the detecting surface of the detector 12 is expressed by R, if $\sin \theta = R/D$ holds, as shown in FIG. 3, the whole cross section of the human body 10 is contained in the field of the detector 12. Therefore, an optimum value of the angle $\theta$ may be determined by $$\theta = \arcsin R/D \tag{2}$$

Accordingly, if the width R of the half of the detector 12 is keyed from the keyboard 42 into the data processing circuit 40, the data processing circuit 40 calculates the angle $\theta$ by using the equation (2), and supplies the result of the calculation through the interface circuit 46 to the motor driving section 48 thereby to rotate the motor 26. Then, the Y-shaped arm 16 is rotated in the B direction in FIG. 1 to set up $\theta$.

By the above-mentioned method, an optimum field can always be obtained. After the distance D and the angle $\theta$ are selected, the motor 36 is rotated and the data obtained by the detector 12 is supplied to the data processing circuit 40 through the interface circuit 38. In the data processing circuit 40, the tomogram is reconstructed on the basis of the data and the reconstructed tomogram is displayed by the display section 44.

Figure 4:
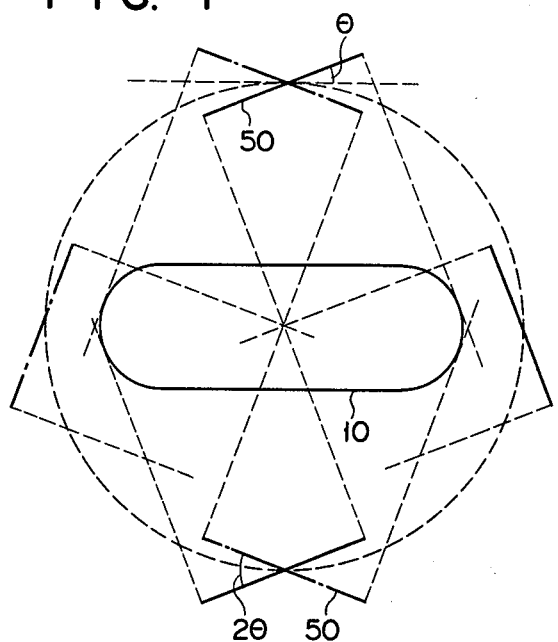

As shown in FIG. 2, when the detector is rotated with an inclination of the detecting surface 50 at an angle $\theta$ with respect to the tangential line, the data of the picture elements on the cross sectional area in all the directions can not be obtained. Thus, the true reconstruction can not be conducted. To solve this problem, the detector 12 is rotated about the human body 10 while the angle $\theta$ is changed. More specifically, as in the previous case, after the detector 12 is rotated about the human body 10 with the detecting surface 50 inclined at angle $\theta$ to the tangential line by 180°, the detector 12 is inclined in an opposite direction to that in the previous case thereby to have an angle $\theta$ of the detecting surface will respect to the tangential line, that is to say, it is rotated by $2\theta$ from the present position, as indicated by a one dot chain line in FIG. 4. Then, it is rotated about the human body by the remaining 180°. In this way, all the directional data in the cross sectional area on the picture elements are obtained, thereby obtaining the true reconstruction tomogram.

Figure 5:
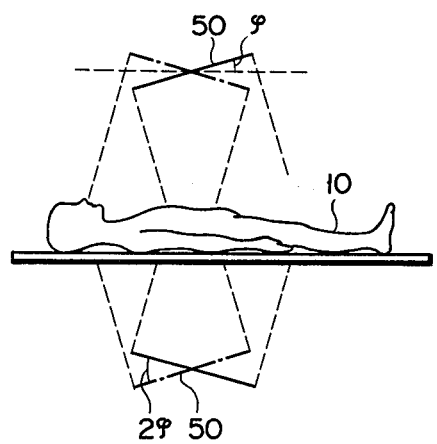

The operation for obtaining a tomogram on the longitudinal cross sectional area taken along the body axis of the human body 10 will be described referring to FIG. 5. In this case, the detector 12 is inclined by the motor 20 so that its surface 50 is inclined at an angle $\phi$ with respect to the body axis. Under this condition, it is rotated about the human body 10. In this way, a portion wider than the field of the detector 12 can be scanned. After the rotation of 180° of the detector 12, it is inclined by $\phi$ in an opposite direction to that of the previous rotation, as indicated by a one dot chain line in FIG. 5, that is, inclined by $2\phi$ from the present position. The angle $\phi$ in this case can also obtain the optimum value, like the angle $\theta$ case.

As described above, according to the present embodiment, the field of the detector 12 can be substantially enlarged by rotating the detector 12 about the human body 10 in a state that the detector 12 is inclined at a given angle with respect to the tangential line of the ring of the rotating rack 28 and the axis of the human body 10. Therefore, the present invention can provide a small-sized, easy-handling emission type CT apparatus.

The present invention is not limited to the above-mentioned embodiment, but may be changed variously within the scope of the present invention. For example, the mechanism to hold and rotate the detector, may variously be modified.

What we claim is:

1. An emission type computed tomography apparatus comprising:
   a detector for producing a signal corresponding to radiation incident on a detecting surface;
   rotating means for rotating said detector in a circle about the body axis of an organism;
   means for interconnecting said detector and said rotating means so that the detecting surface may have any desired angle with respect to a tangential line of the motion of said detector, said interconnecting means including a member for moving said detector toward and away from said organism;
   processing means for determining first a fixed diameter of the circular motion of said detector orthogonal to the body axis in accordance with the body width of the organism and second, an angle of the detecting surface with respect to said tangential line in accordance with the determined diameter and the size of the detecting surface of said detector such that a field of the detector includes the body axis and a center of the field does not pass through the body axis, and for processing an output signal from said detector over the motion of said detector caused by said rotating means.

2. An emission type computed tomography apparatus according to claim 1, in which said interconnecting means has an arm for supporting said detector so that the detecting surface may be disposed at a desired angle with respect to the body axis, and a holding rod for holding said detector through said arm.

* * * * *